(12) United States Patent
Chen et al.

(10) Patent No.: US 10,465,075 B2
(45) Date of Patent: Nov. 5, 2019

(54) METHOD OF PREPARING CORE-SHELL ZINC OXIDE PARTICLES

(71) Applicant: Pan-Continental Chemical Co., Ltd., Taipei (TW)

(72) Inventors: Chia-Ming Chen, Taichung (TW); Kuan-Yi Wang, Taichung (TW); Hwei-Hwang Chiou, Taichung (TW)

(73) Assignee: PAN-CONTINENTAL CHEMICAL CO., LTD., Taipei (TW)

( * ) Notice: Subject to any disclaimer, the term of this patent is extended or adjusted under 35 U.S.C. 154(b) by 0 days.

(21) Appl. No.: 16/103,092

(22) Filed: Aug. 14, 2018

(65) Prior Publication Data

US 2019/0055407 A1 Feb. 21, 2019

(30) Foreign Application Priority Data

Aug. 18, 2017 (TW) .............................. 106128053 A (51) Int. Cl.
| | |
|---|---|
| *C09C 1/02* | (2006.01) |
| *A61K 8/27* | (2006.01) |
| *A61Q 17/04* | (2006.01) |
| *A61K 8/02* | (2006.01) |

(52) U.S. Cl.
CPC ............ *C09C 1/024* (2013.01); *A61K 8/0241* (2013.01); *A61K 8/27* (2013.01); *A61Q 17/04* (2013.01); *C09C 1/025* (2013.01); *A61K 2800/621* (2013.01); *A61K 2800/651* (2013.01); *C01P 2004/61* (2013.01)

(58) Field of Classification Search
None
See application file for complete search history.

(56) References Cited

U.S. PATENT DOCUMENTS

| | | | | |
|---|---|---|---|---|
| 7,635,729 | B2 * | 12/2009 | Nip ........................ | C08K 9/02 |
| | | | | 428/403 |
| 2007/0072959 | A1 | 3/2007 | Nip | |

FOREIGN PATENT DOCUMENTS

| | | |
|---|---|---|
| CN | 106279762 A | 1/2017 |
| JP | 3849177 B2 | 11/2006 |
| TW | 201638012 A | 11/2016 |

OTHER PUBLICATIONS

Database WPI; Week 201720; Thomson Scientific, London, GB ; AN 2017-12745G ; XP002778453 & TW201638012 A (Pan-Continental Chem Co Ltd) Nov. 1, 2016 (Nov. 1, 2006).
Database WPI; Week 201721; Thomson Scientific, London, GB ; AN 2017-09817Q ; XP002778454 & CN106279762 A (Pan-Continental Chem Co Ltd) Jan. 4, 2017 (Jan. 4, 2007).
Search Report issued to European counterpart application No. 17208153.1 by the EPO dated Mar. 2, 2018.
Office Action issued to Korean counterpart application No. 10-2018-0096218 by the KIPO dated Aug. 2, 2019 (4 pages).

* cited by examiner

*Primary Examiner* — Brian J Davis
(74) *Attorney, Agent, or Firm* — Hamre, Schumann, Mueller & Larson, P.C.

(57) ABSTRACT

A method of preparing core-shell zinc oxide particles, includes: mixing a calcium-containing material with a first zinc ammonia complex salt solution; heating the thus obtained first mixture to remove ammonia, thereby obtaining a first intermediate product; mixing the first intermediate product with a second zinc ammonia complex salt solution to obtain a second mixture; heating the second mixture to remove ammonia, followed by conducting a drying process to obtain a second intermediate product; and calcining the second intermediate product to obtain the core-shell zinc oxide particles. A core-shell zinc oxide particle is prepared by the aforementioned method, and a composition for shielding ultraviolet light includes the core-shell zinc oxide particles.

13 Claims, 8 Drawing Sheets

METHOD OF PREPARING CORE-SHELL ZINC OXIDE PARTICLES

CROSS-REFERENCE TO RELATED APPLICATION

This application claims priority of Taiwanese Invention Patent Application No. 106128053, filed on Aug. 18, 2017.

FIELD

This disclosure relates to zinc oxide particles and a method of making the same, and more particularly to a method of preparing core-shell zinc oxide particles.

BACKGROUND

A variety of materials have been used to absorb ultraviolet (UV) light and thus help to protect against UV radiation. For example, titanium dioxide ($TiO_2$) is the most commonly used material for absorbing UV light. However, titanium dioxide is only effective in absorbing UVB, but not UVA, which is more difficult to be protected among all UV wavelengths and is known as a leading cause of human skin cancer.

In order to solve the aforementioned problem, materials that are effective in shielding UV light (i.e. reflecting UV light), such as zinc oxide that is capable of shielding both UVA and UVB, has been utilized to protect against UV radiation. However, due to the high polarity of zinc oxide, its powdered form is often agglomerated and hardly dispersed. One way to solve such problem is to modify the physicochemical properties of zinc oxide powder.

For example, Taiwanese Invention patent No. 1546260 discloses core-shell zinc oxide particles having improved dispersibility, which includes a core of calcium carbonate material and a shell layer of zinc oxide flakes. US patent publication No. 2007/0072959 A1 discloses composite particles in which zinc oxide is formed on a particle core that includes silica, clay, talc, mica, activated carbon and carbon black, and/or in which the zinc oxide is co-precipitated as a coating or intermixed with other particles.

Although the conventional core-shell zinc oxide particles as mentioned above have improved dispersibility, none of the them has been used as a ultraviolet light protection material. Therefore, the applicants endeavor to prepare core-shell zinc oxide particles having excellent UV light-shielding effect.

SUMMARY

Therefore, an object of the present disclosure is to provide a method of preparing core-shell zinc oxide particles that can alleviate at least one of the drawbacks of the prior art.

According to this disclosure, the method of preparing core-shell zinc oxide particles includes:

mixing a calcium-containing material with a first zinc ammonia complex salt solution to obtain a first mixture;

heating the first mixture to remove ammonia, thereby obtaining a first intermediate product;

mixing the first intermediate product with a second zinc ammonia complex salt solution to obtain a second mixture;

heating the second mixture to remove ammonia, followed by conducting a drying process to obtain a second intermediate product; and calcining the second intermediate product to obtain core-shell zinc oxide particles.

A second object of this disclosure is to provide a core-shell zinc oxide particle prepared by the aforementioned method.

A third object of this disclosure, is to provide a composition for shielding UV light. The composition includes the aforementioned core-shell zinc oxide particles.

BRIEF DESCRIPTION OF THE DRAWINGS

Other features and advantages of the disclosure will become apparent in the following detailed description of the embodiment(s) with reference to the accompanying drawings, of which.

DETAILED DESCRIPTION

Before the disclosure is described in greater detail, it should be noted that where considered appropriate, reference numerals or terminal portions of reference numerals have been repeated among the figures to indicate corresponding or analogous elements, which may optionally have similar characteristics.

In order to prepare core-shell zinc oxide particles having excellent UV light-shielding effect, the applicants have found that, by heating a mixture of a calcium-containing material and a zinc ammonia complex salt solution to remove ammonia, and heating a mixture of the first intermediate product thus formed and another zinc ammonia complex salt solution to further remove ammonia, follow by conducting calcination, the obtained core-shell zinc oxide particles are capable to reflect more UV light as compared with those obtained by the conventional preparation method, in which the zinc ammonia complex salt solution was added once and the heating step was also conducted once.

Therefore, a method of preparing core-shell zinc oxide particles provided in this disclosure includes the following steps S1-S5.

In Step S1, a calcium-containing material is mixed with a first zinc ammonia complex salt solution to obtain a first mixture.

In Step S2, the first mixture is heated to remove ammonia, thereby obtaining a first intermediate product.

In Step S3, the first intermediate product is mixed with a second zinc ammonia complex salt solution to obtain a second mixture.

In Step S4, the second mixture is heated to remove ammonia, followed by conducting a drying process to obtain a second intermediate product.

In Step S5, the second intermediate product is calcined to obtain core-shell zinc oxide particles.

According to this disclosure, the calcium-containing material should not decompose during the heating steps and the calcination step and may include but is not limited to, calcium carbonate-containing material, calcium oxide-containing material, calcium silicate-containing material, calcium chloride-containing material, calcium sulfate-containing material, and combinations thereof.

Examples of the calcium carbonate-containing material suitable for use in this disclosure include, but are not limited to, montmorillonite, kaolinite, diatomaceous earth, marble powder, and combinations thereof. In certain embodiments, the calcium-containing material is marble powder having an average particle size ranging from 5 μm to 7 μm.

In certain embodiments, in step S1 and step S3, each of the first and second zinc ammonia complex salt solutions has a zinc ion concentration ranging from 8 wt % to 20 wt %. In certain embodiments, each of the first and second zinc ammonia complex salt solutions has a zinc ion concentration ranging from 8 wt % to 11 wt %.

In certain embodiments, in step S1, the first zinc ammonia complex salt solution is a zinc ammonia bicarbonate complex salt solution. In certain embodiments, the first zinc ammonia complex salt solution is a $Z_n(NH_3)_n(HCO_3)_2$ solution, wherein n is an integer of 1 to 6.

In certain embodiments, in step S3, the second zinc ammonia complex salt solution is a zinc ammonia bicarbonate complex salt solution. In certain embodiments, the second zinc ammonia complex salt solution is a $Z_n(NH_3)_n(HCO_3)_2$ solution, wherein n is an integer of 1 to 6.

In certain embodiments, the weight ratio of the first zinc ammonia complex salt solution to the second zinc ammonia complex salt solution may range from 1/3 to 3/1. In certain embodiments, the weight ratio of the first zinc ammonia complex salt solution to the second zinc ammonia complex salt solution ranges from 1/3 to 3/5. In other embodiments, the weight ratio of the first zinc ammonia complex salt solution to the second zinc ammonia complex salt solution ranges from 5/3 to 3/1. In particular, when the weight ratio of the first zinc ammonia complex salt solution to the second zinc ammonia complex salt solution ranges from 1/3 to 3/5 or 5/3 to 3/1, the obtained core-shell zinc oxide particles have improved UV light-shielding effect.

It should be noted that the heating conditions (such as the removal rate, time period, temperature, etc.) for each step may vary depending on the needs of the user and implementation requirements, so as to achieve the desired effect.

In certain embodiments, heating of the first mixture and heating of the second mixture may be individually conducted at an ammonia removal rate ranging from 0.02%/min to 0.09%/min.

According to the disclosure, the aforesaid ammonia removal rate (%/min) is calculated based on the following equation <I>:

$$\text{Ammonia removal rate} = (A-B)/C \qquad <\text{I}>$$

where A=The ammonia concentration (%) of a product, i.e., the weight percent of ammonia in the first or second mixture based on the total weight of the first or second mixture, before the heating step B=The ammonia concentration (%) of the product after the heating step C=The time period of the heating step (min)

In certain embodiments, heating of the first mixture and heating of the second mixture may also remove carbon dioxide produced therefrom, in which a carbon dioxide removal rate may range from 0.04 (g/L)/min to 0.8 (g/L)/min.

According to the disclosure, the aforesaid carbon dioxide removal rate ((g/L)/min) is calculated based on the following equation <II>:

$$\text{Carbon dioxide removal rate} = (D-E)/F \qquad <\text{II}>$$

where D=The carbon dioxide concentration of a product (g/L), i.e., the weight of carbon dioxide per liter of the first mixture or the second mixture, before the heating step E=The carbon dioxide concentration (g/L) of the product after the heating step F=The time period of the heating step (min)

It should be noted that, when the aforesaid ammonia removal rate is not within the range of 0.02%/min to 0.09%/min, and/or when the aforesaid carbon dioxide removal rate is not within the range of 0.04 (g/L)/min to 0.8 (g/L)/min, the first intermediate product and/or the second intermediate product thus obtained may be less stable.

According to the disclosure, the first mixture and the second mixture are individually heated at a temperature ranging from 80° C. to lower than 100° C. In certain embodiments, the first mixture and the second mixture are individually heated at a temperature ranging from 85° C. to 95° C.

In certain embodiments, the weight ratio of the zinc of the first zinc ammonia complex salt solution to the calcium-containing material ranges from about 0.08 to about 1.41.

In certain embodiments, the weight ratio of the total zinc of the first and second zinc ammonia complex salt solutions to the calcium-containing material ranges from about 0.34 to about 1.88.

In certain embodiments, the Step S5 may be conducted at a temperature ranging from 340° C. to 360° C. In certain embodiments, the Step S5 may be conducted for 50 to 70 mins.

In certain embodiments, the first intermediate product formed in Step S2 includes a core of the calcium-containing material and zinc carbonate flakes formed on the core. The zinc carbonate flakes are substantially parallel to the surface of the core.

In certain embodiments, the core-shell zinc oxide particles prepared by the method of the present disclosure include a core of the calcium-containing material and a shell of zinc oxide flakes formed on the core in which a portion of the zinc oxide flakes are not parallel to the other portion of zinc oxide flakes.

As compared to the particles having zinc oxide flakes formed on the core and substantially parallel to the surface of the core (i.e., those prepared by the conventional process that is substantially the same as Steps S1, S2 and S5 of this disclosure, the core-shell zinc oxide particles prepared by the method of the present disclosure including the aforesaid Steps S1 to S5 would have significantly more zinc oxide flakes (which may not be parallel to each other) that would increase the light reflective area, thereby improving the light shielding effect thereof upon exposure to the ultraviolet light.

In certain embodiments, the core-shell zinc oxide particles may have an average particle size in the range of 6 μm to 11 μm.

Since the core-shell zinc oxide particles prepared by the method of this disclosure have been proven to be effective in reflecting UV light, the core-shell zinc oxide particles according to this disclosure may be expected to have potent UV light-shielding effect. Accordingly, this disclosure also provides a composition for shielding UV light, including the aforesaid core-shell zinc oxide particles.

In certain embodiments, the composition may further include an UV light-absorbing material or an UV light-reflecting material.

The disclosure will be further described by way of the following examples and comparative example. However, it should be understood that the following examples and comparative example are solely intended for the purpose of illustration and should not be construed as limiting the disclosure in practice.

EXAMPLES

Preparation of Zinc Ammonia Complex Salt Solutions

A zinc-containing waste produced from the metal industry was mixed with an aqueous solution comprising ammonium hydroxide and carbon dioxide in a container (the weight ratio of zinc:ammonia:carbon dioxide in the resultant mixture is 10 g/L: 7-12 g/L: 7-9 g/L) to dissolve the zinc, followed by removing the heavy metals contained therein to form a zinc ammonia complex salt solution having a zinc ion concentration of 9.55 wt %, in which the zinc ammonia complex salt was $Zn(NH_3)_n(HCO_3)_2$, and n is an integer of 1 to 6.

Preparation of the Core-Shell Zinc Oxide Particle

Examples 1 to 5 (E1-E5)

The core-shell zinc oxide particles of Examples 1 to 5 were prepared according to the following steps.

Step S1: mixing 221 g of a calcium-containing material (i.e., marble powder) having an average particle diameter of about 6 μm with a given amount of the zinc ammonia complex salt solution obtained above in a 4 L beaker under agitation, so as to obtain a first mixture.

Step S2: heating the first mixture at 90° C. for 3 hours to remove ammonia and carbon dioxide under an ammonia removal rate ranging from 0.025±0.001%/min to 0.03±0.001%/min and a carbon dioxide removal rate ranging from 0.05±0.01 (g/L)/min to 0.25±0.01 (g/L)/min, thereby obtaining a first intermediate product. The first intermediate product thus obtained has a core of the calcium-containing material and zinc carbonate flakes formed on the core.

Step S3: mixing the first intermediate product with a further given amount of the zinc ammonia complex salt solution obtained above under agitation to obtain a second mixture.

Step S4: heating the second mixture at 90° C. to remove ammonia and carbon dioxide under an ammonia removal rate ranging from 0.025±0.001%/min to 0.085±0.001%/min and a carbon dioxide removal rate ranging from 0.25±0.01 (g/L)/min to 0.75±0.01 (g/L)/min. The product thus obtained was then filtered to remove water, followed by washing with 3 L of water and drying in a 100° C. oven for 4 hours, so as to obtain a second intermediate product.

Step S5: calcining the second intermediate product at 350° C. for 60 minutes to convert zinc carbonate to zinc oxide, thereby obtaining the core-shell zinc oxide particles. Each of the core-shell zinc oxide particles of E1-E5 includes a core of the calcium-containing material and a shell of zinc oxide flakes formed on the core.

The amount of the zinc ammonia complex salt solutions used in Steps S1 and S3 of these examples and the weight of zinc in the zinc ammonia complex salt solution used in Step S1 to that of the calcium-containing material are respectively listed in Table 1. The total zinc weight of the zinc ammonia complex salt solutions used in Steps S1 and S3 to the weight of the calcium-containing material was about 0.3457.

TABLE 1

|    | Amount of the zinc ammonia complex salt solution in Step S1 (g) | Amount of the zinc ammonia complex salt solution in Step S3 (g) | The weight ratio of zinc in the zinc ammonia complex salt solution used in Step S1 to that of the calcium-containing material (w/w) |
|----|------|------|------------------------|
| E1 | 200  | 600  | 19.1/221 (about 0.0864) |
| E2 | 300  | 500  | 28.65/221 (about 0.1296) |
| E3 | 400  | 400  | 38.2/221 (about 0.1729) |
| E4 | 500  | 300  | 47.75/221 (about 0.2161) |
| E5 | 600  | 200  | 57.3/221 (about 0.2593) |

Examples 6 to 10 (E6-E10)

The core-shell zinc oxide particles of E6-E10 were made by procedures respectively similar to those of E1-E5, except that the amount of the marble powder used in E6-E10 was 40.7 g. In these examples, the weight ratio of zinc in the zinc ammonia complex salt solution used in Step S1 of E6-E10 to that of the calcium-containing material is respectively listed in Table 2, and the total zinc weight of the zinc ammonia complex salt solutions used in Steps S1 and S3 to that of the calcium-containing material was about 1.8771.

TABLE 2

|     | The weight ratio of zinc in the zinc ammonia complex salt solution used in Step S1 to that of the calcium-containing material (w/w) |
|-----|-----------------------------------|
| E6  | 19.1/40.7 (about 0.4693)          |
| E7  | 28.65/40.7 (about 0.7039)         |
| E8  | 38.2/40.7 (about 0.9386)          |
| E9  | 47.75/40.7 (about 1.1732)         |
| E10 | 57.3/40.7 (about 1.4079)          |

Comparative Example 1 (CE1)

The core-shell zinc oxide particles of comparative example 1 were prepared according to the following steps.

Step 1: mixing the calcium-containing material (marble powder) having an average particle diameter of about 6 μm (221 g) and the zinc ammonia complex salt solution obtained above (800 g, equal to the total amount of the zinc ammonia complex salt solution used in Steps S1 and S3 of E1-E10) in a 4 L beaker under agitation, so as to obtained a first mixture.

Step 2: heating the first mixture at 90° C. for six hours to remove ammonia and carbon dioxide under an ammonia removal rate ranging from 0.025±0.001%/min to 0.03±0.001%/min and a carbon dioxide removal rate ranging from 0.05±0.01 (g/L)/min to 0.32±0.01 (g/L)/min. The product thus obtained was filtered to remove water, washed with 3 L of water, and then dried in an oven at 100° C. for 4 hours, so as to obtain an intermediate product having zinc carbonate coated on the calcium-containing material.

Step 3: calcining the obtained intermediate product at 350° C. for 60 minutes to convert zinc carbonate to zinc oxide, thereby obtaining the core-shell zinc oxide particles, each of the particle includes a core of the calcium-containing material and a shell of zinc oxide flakes formed on the core.

Evaluation of the Ultraviolet Light-Shielding Effect of Core-Shell Zinc Oxide Particles Methods:

A. UV-VIS Absorption Spectrum

The core-shell zinc oxide particles of each of E1-E5 and CE1 were filled in a sample cell having a diameter of about 3 cm, and the filling thickness of the core-shell zinc oxide particles was about 1 cm. One side of the sample cell is a transparent glass, allowing light to pass through.

Figure 1:
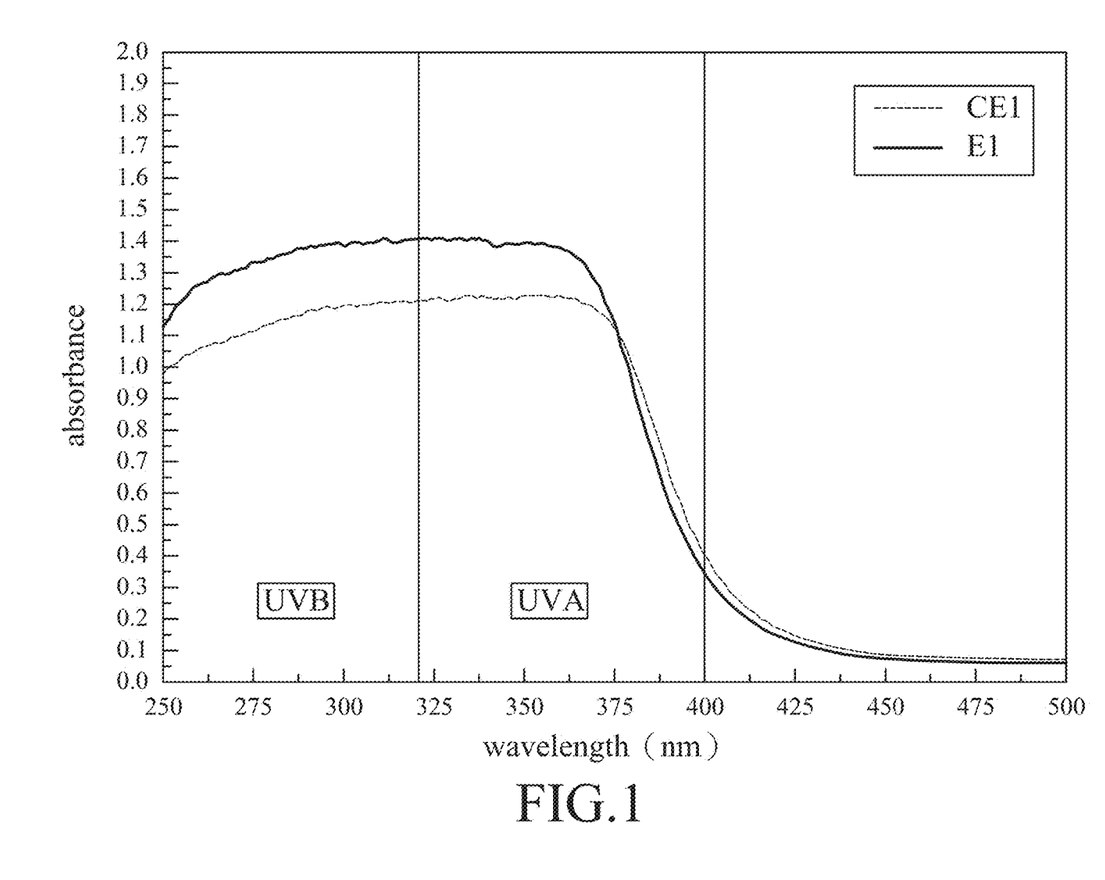
FIG. 1 shows the UV-Visible (VIS) absorbance spectrum of the core-shell zinc oxide particles of Comparative Example 1 (CE1) and Example 1 (E1)
Figure 2:
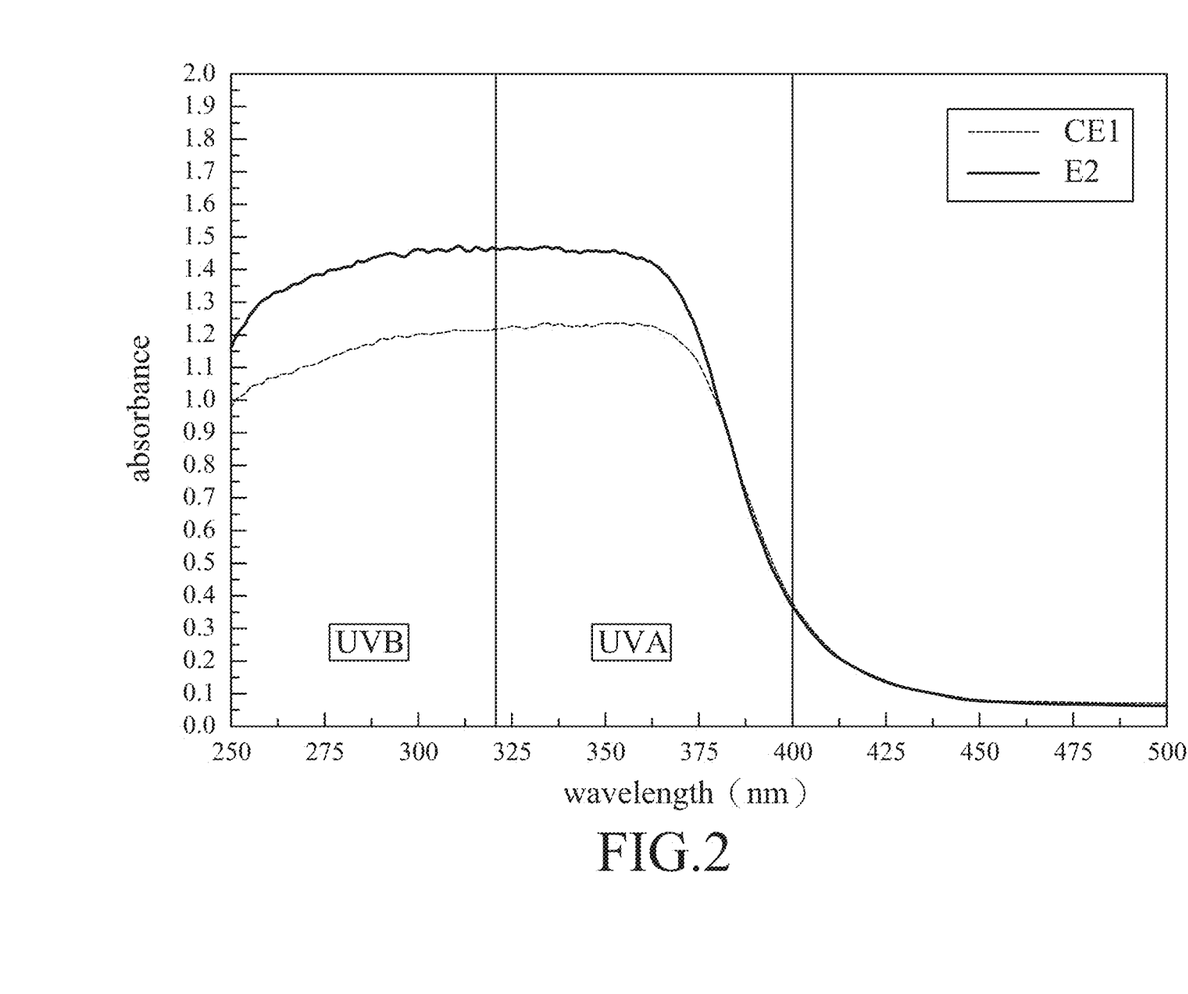
FIG. 2 shows the UV-VIS absorbance spectrum of the core-shell zinc oxide particles of CE1 and Example 2 (E2)
Figure 3:
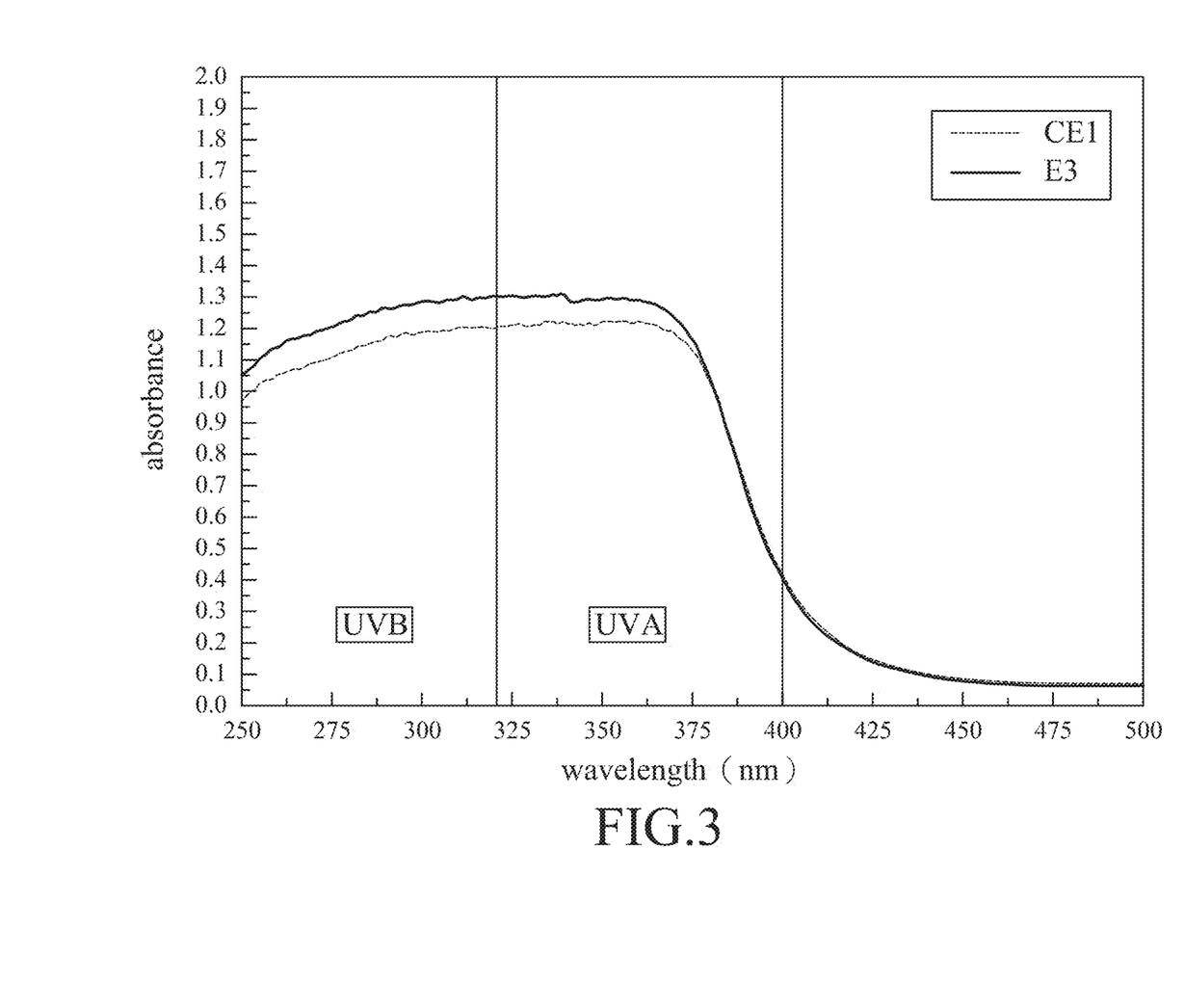
FIG. 3 shows the UV-VIS absorbance spectrum of the core-shell zinc oxide particles of CE1 and Example 3 (E3)
Figure 4:
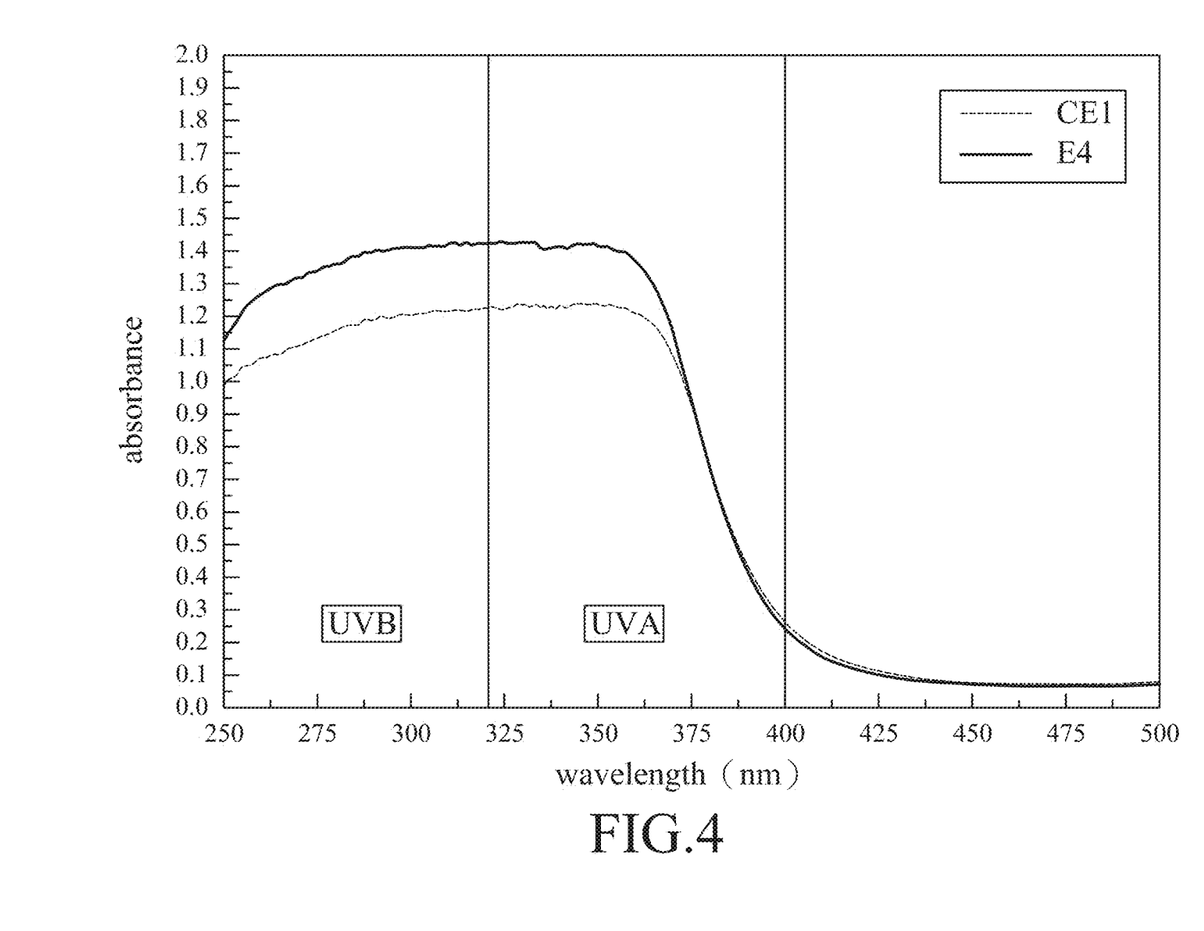
FIG. 4 shows the UV-VIS absorbance spectrum of the core-shell zinc oxide particles of CE1 and Example 4 (E4)
Figure 5:
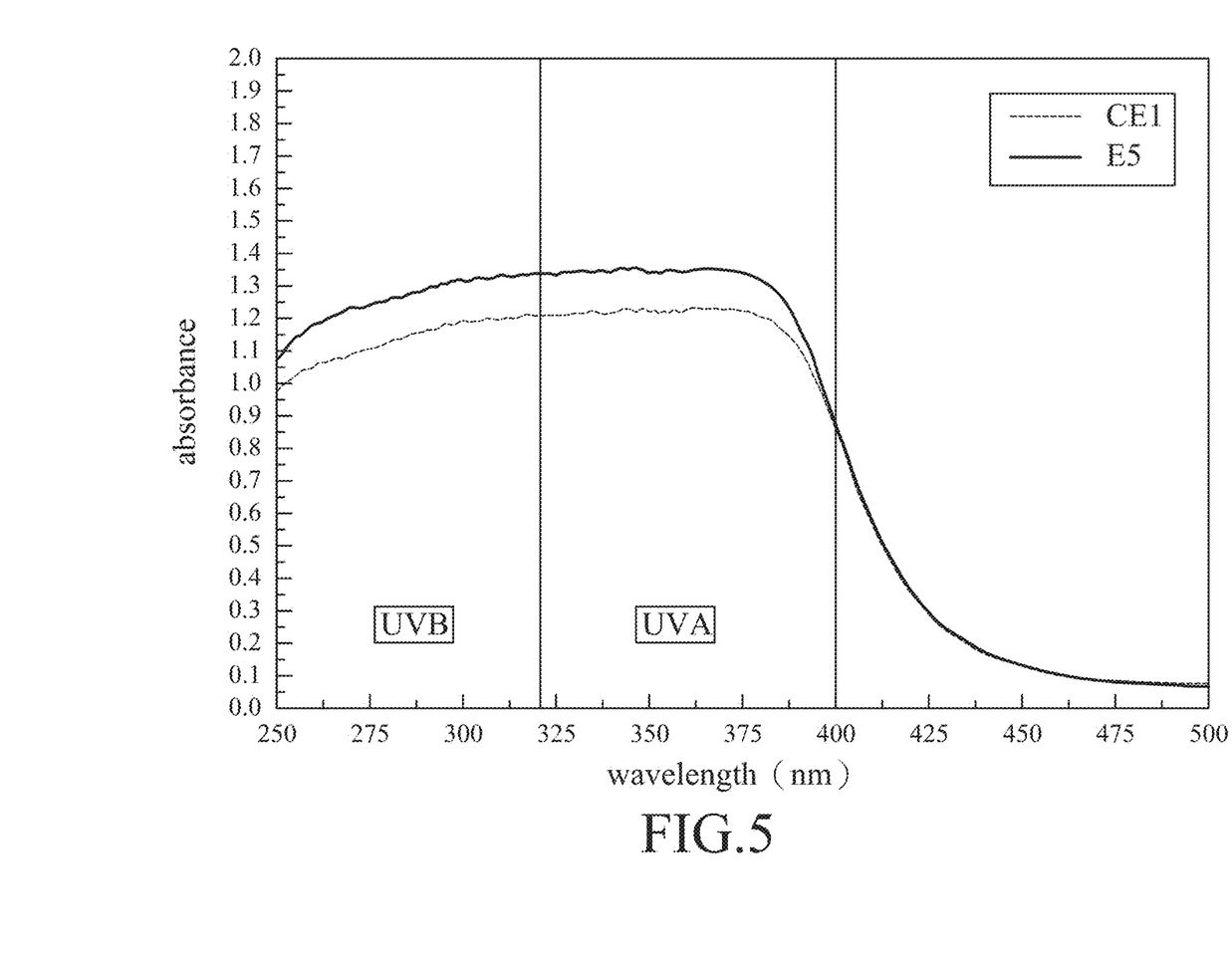
FIG. 5 shows the a UV-VIS absorbance spectrum of the core-shell zinc oxide particles of CE1 and Example 5 (E5)

The sample cell filled with the core-shell zinc oxide particles was placed in a UV-VIS spectrophotometer (HITACHI 3900), and then scanned from 500-250 nm at a scanning speed of 600 nm/min to measure the transmittance of light passing through the core-shell zinc oxide particles of each example. The obtained transmittance was then converted to absorbance values from which the UV-VIS absorbance spectrum was depicted (see FIGS. 1-5). A higher absorbance value (i.e., the lower transmittance) indicates that the core-shell zinc oxide particles can reflect more UV light and thus has a stronger UV light-shielding effect.

B. Increased Percentage of Ultraviolet Absorbance

The maximum UV absorbance value of the core-shell zinc oxide particles of E1-E5 and CE1 at a wavelength ranging from 340 to 360 nm were obtained from the respective UV-VIS light absorption spectrum. An increased percentage of UV absorbance in each of E1-E5 was calculated according to the following equation <III>, and the obtained result was shown in Table 3.

$$G=[(H-I)/I]\times 100\% \quad <III>$$

where G=Increased percentage of UV absorbance (%)
H=The maximum UV absorbance value of each example
I=The maximum UV absorbance value of CE 1

Results:

TABLE 3

| | The weight ratio of the zinc ammonia complex salt solutions used in Step S1 and Step S3 | The increased percentage of UV absorbance (%) |
|---|---|---|
| E1 | 1/3 | 14.8 |
| E2 | 3/5 | 19.0 |
| E3 | 1/1 | 7.0 |
| E4 | 5/3 | 16.4 |
| E5 | 3/1 | 10.0 |

FIGS. 1 to 5 respectively show the UV-Visible (VIS) absorbance spectrum of the core-shell zinc oxide particles of E1 to E5 in comparison with that of CE1. It can be seen from Table 3 and FIGS. 1 to 5 that the absorbance of each of E1-E5, either within the entire UVB region or most of the UVA region, is higher than that of CE1, that is, the core-shell zinc oxide particles of each of E1-E5 can reflect more UV light than those of CE1. The results indicate that under the same amount of zinc ammonia complex salt solution, the core-shell zinc oxide particles prepared by the method of the present disclosure (i.e., addition of the zinc ammonia complex salt solution by two separate steps) had better UV light-shielding effect than those prepared by the conventional method (i.e., addition of all the zinc ammonia complex salt solution in a single step).

In addition, Table 3 also shows that when the weight ratio of the zinc ammonia complex salt solutions used in Step S1 and S3 ranges from 1/3 to 3/5 and 5/3 to 3/1, the obtained core-shell zinc oxide particles can exhibit at least 10% increase of UV absorbance, i.e., a better UV light-shielding effect.

Analysis of the Microstructure of the Core-Shell Zinc Oxide Particle

Figure 6:
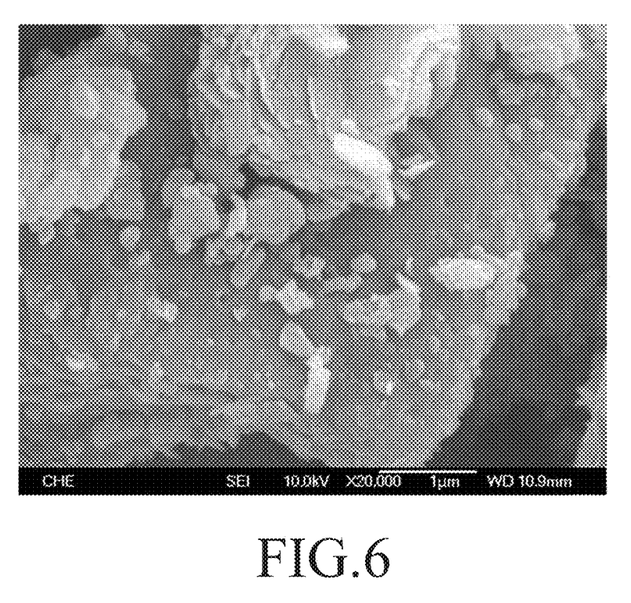
FIG. 6 is a scanning electron microscope (SEM) image showing the microstructure of the core-shell zinc oxide particles of CE1.
Figure 7:
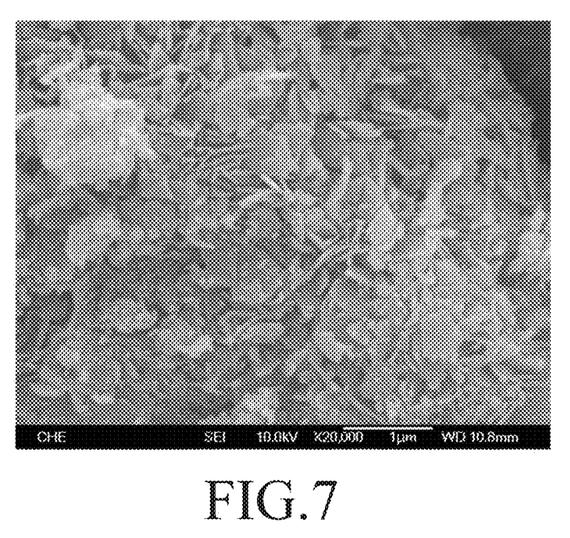
FIG. 7 is a SEM image showing the microstructure of the core-shell zinc oxide particles of E1.
Figure 8:
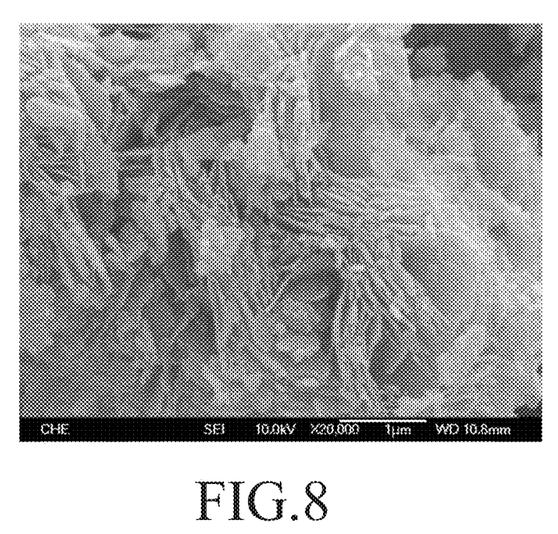
FIG. 8 is a SEM image showing the microstructure of the core-shell zinc oxide particles of E2.
Figure 9:
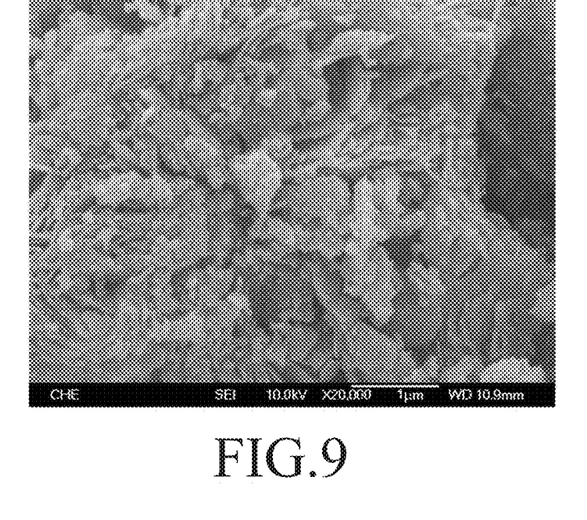
FIG. 9 is a SEM image showing the microstructure of the core-shell zinc oxide particles of E3.
Figure 10:
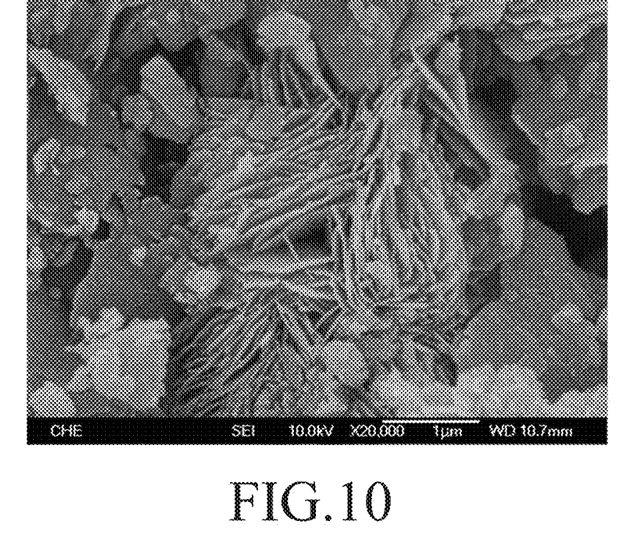
FIG. 10 is a SEM image showing the microstructure of the core-shell zinc oxide particles of E5.

Methods:

The core-shell zinc oxide particles of each of CE1, E1-E3 and E5 were photographed using scanning electron microscope (SEM). The obtained SEM images of CE1, E1-E3 and E5 were respectively shown in FIGS. 6 to 10.

Results:

As shown in FIGS. 7 to 10, the core-shell zinc oxide particles of each of E1-E3 and E5 included a plurality of zinc oxide flakes. By comparing FIG. 6 with FIGS. 7 to 10, it can be seen that the amount of zinc oxide flakes which are not parallel to the core surface of the core-shell zinc oxide particles of E1-E3 and E5, is greater than that of CE1. That is, the core-shell zinc oxide particles of E1-E3 and E5 have larger light reflective areas on the shell of the particles than those of CE1. These results indicate that the core-shell zinc oxide particles prepared by the method of the present disclosure (i.e., addition of the zinc ammonia complex salt solution by two separate steps) had better UV light-shielding effect compared to those prepared by the conventional method (i.e., addition of all the zinc ammonia complex salt solution in a single step).

In conclusion, by virtue of dividing the addition of zinc ammonia complex salt solution into two separate steps, the core-shell zinc oxide particles prepared by the method of this disclosure may have better UV light-shielding effect.

In the description above, for the purposes of explanation, numerous specific details have been set forth in order to provide a thorough understanding of the embodiment(s). It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects, and that one or more features or specific details from one embodiment may be practiced together with one or more features or specific details from another embodiment, where appropriate, in the practice of the disclosure.

While the disclosure has been described in connection with what is (are) considered the exemplary embodiment(s), it is understood that this disclosure is not limited to the disclosed embodiment(s) but is intended to cover various arrangements included within the spirit and scope of the broadest interpretation so as to encompass all such modifications and equivalent arrangements.

What is claimed is:

1. A method of preparing core-shell zinc oxide particles comprising the steps of:

mixing a calcium-containing material with a first zinc ammonia complex salt solution to obtain a first mixture;

heating the first mixture to remove ammonia, thereby obtaining a first intermediate product;

mixing the first intermediate product with a second zinc ammonia complex salt solution to obtain a second mixture;

heating the second mixture to remove ammonia, followed by conducting a drying process to obtain a second intermediate product; and calcining the second intermediate product to obtain the core-shell zinc oxide particles.

2. The method as claimed in claim 1, wherein the step of calcining the second intermediate product is conducted at a temperature ranging from 340° C. to 360° C.

3. The method as claimed in claim 1, wherein the step of heating the first mixture and the step of heating the second mixture are individually conducted at an ammonia removal rate ranging from 0.02 wt %/min to 0.09 wt %/min.

4. The method as claimed in claim 1, wherein the first mixture and the second mixture are individually heated at a temperature ranging from 80° C. to lower than 100° C.

5. The method as claimed in a claim 1, wherein each of the first and second zinc ammonia complex salt solutions has a zinc ion concentration ranging from 8 wt % to 20 wt %.

6. The method as claimed in claim 1, wherein the weight ratio of the first zinc ammonia complex salt solution to the second zinc ammonia complex salt solution ranges from 1/3 to 3/1.

7. The method as claimed in claim 1, wherein the first intermediate product includes a core of the calcium-containing material and zinc carbonate flakes formed on the core.

8. The method as claimed in claim 7, wherein the first zinc ammonia complex salt solution is a zinc ammonia bicarbonate complex salt solution.

9. The method as claimed in claim 1, wherein the core-shell zinc oxide particles include a core of the calcium-containing material and a shell of zinc oxide flakes formed on the core.

10. The method as claimed in claim 9, wherein the second zinc ammonia complex salt solution is a zinc ammonia bicarbonate complex salt solution.

11. The method as claimed in claim 1, wherein the calcium-containing material is selected from the group consisting of calcium carbonate-containing material, calcium oxide-containing material, calcium silicate-containing material, calcium chloride-containing material, calcium sulfate-containing material, and combinations thereof.

12. A core-shell zinc oxide particle, which is prepared by the method as claimed in claim 1.

13. A composition for shielding ultraviolet light, comprising the core-shell zinc oxide particles as claimed in claim 12.

* * * * *